US00PP35886P2

(12) United States Plant Patent
Tuszyński

(10) Patent No.: US PP35,886 P2
(45) Date of Patent: Jun. 25, 2024

(54) ***CORDYLINE* PLANT NAMED 'TUS020'**

(50) Latin Name: *Cordyline australis*
Varietal Denomination: TUS020

(71) Applicant: Grzegorz Tuszyński, Otrebusy (PL)

(72) Inventor: Grzegorz Tuszyński, Otrebusy (PL)

( * ) Notice: Subject to any disclaimer, the term of this patent is extended or adjusted under 35 U.S.C. 154(b) by 0 days.

(21) Appl. No.: 18/229,017

(22) Filed: Aug. 1, 2023

(51) Int. Cl.
*A01H 6/12* (2018.01)
*A01H 5/12* (2018.01)

(52) U.S. Cl.
USPC ..... Plt./383

(58) Field of Classification Search
USPC ..... Plt./383
CPC ..... A01H 6/12; A01H 5/12
See application file for complete search history.

*Primary Examiner* — Keith O. Robinson
(74) *Attorney, Agent, or Firm* — Cassandra Bright

(57) ABSTRACT

A new and distinct *Cordyline australis* plant named 'TUS020' is disclosed, characterized by striking green leaves with creamy white margins, fading to pink and red toward the main stem. Foliage retains its coloring year-round. Plants are compact, with round, upright, arching habits. The new cultivar is a *Cordyline*, typically suited for ornamental container and landscape use.

3 Drawing Sheets

Latin name of the genus and species: *Cordyline australis*.
Variety denomination: 'TUS020'.

BACKGROUND OF THE INVENTION

The new cultivar is the result of a naturally occurring mutation of the parent variety, *Cordyline australis* 'Sundance', unpatented. The discovery of the new variety was made in March of 2019 by the inventor in Otrebusy, Poland.

Asexual reproduction of the new cultivar 'TUS020' was first performed in Otrebusy, Poland by tissue culture in 2019. 'TUS020' has since produced several generations and has shown that the unique features of this cultivar are stable and reproduced true to type.

SUMMARY OF THE INVENTION

The cultivar 'TUS020' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TUS020'. These characteristics in combination distinguish 'TUS020' as a new and distinct *Cordyline* cultivar:

1. Green leaves with creamy white edges, fading into pink towards the bottom, and ending in red at the main stem.
2. Foliage retains its coloring year-round.
3. Compact.

PARENTAL COMPARISON

Plants of the new cultivar 'TUS020' are similar to the parent variety in most horticultural characteristics. However, 'TUS020' differs in the following:

1. Foliage of the new variety is green with creamy white edges, fading into pink towards the bottom, and ending in bright pink/red at the main stem. Foliage of the parent is green with a pale reddish main stem.

COMMERCIAL COMPARISON

Plants of the new cultivar 'TUS020' are similar to the commercial variety *Cordyline australis* 'Red Heart', unpatented, in most horticultural characteristics. However, 'TUS020' differs in the following:

1. Foliage of the new variety is darker green than foliage of this comparator.
2. Foliage of the new variety has white margins, while foliage of this comparator does not.
3. Foliage of the new variety is narrower than foliage of this comparator.

Plants of the new cultivar 'TUS020' are similar to the commercial variety *Cordyline australis* 'Torbay Dazzler', unpatented, in most horticultural characteristics. However, 'TUS020' differs in the following:

1. Foliage of the new variety has a red base, while foliage of this comparator does not.

Plants of the new cultivar 'TUS020' are similar to the commercial variety *Cordyline australis* 'Variegate', unpatented, in most horticultural characteristics. However, 'TUS020' differs in the following:

1. Foliage of the new variety has a red base, while foliage of this comparator does not.

BRIEF DESCRIPTION OF THE PHOTOGRAPHS

The accompanying photographs illustrates in full color a typical plant and foliage of 'TUS020' grown in a greenhouse in Wernhout, the Netherlands. This plant is approximately 12 to 18 months old, grown in a 28 cm pot. The photographs were taken using conventional techniques and although colors may appear different from actual colors due to light reflectance it is as accurate as possible by conventional photographic techniques.

DETAILED BOTANICAL DESCRIPTION

Figure 1:
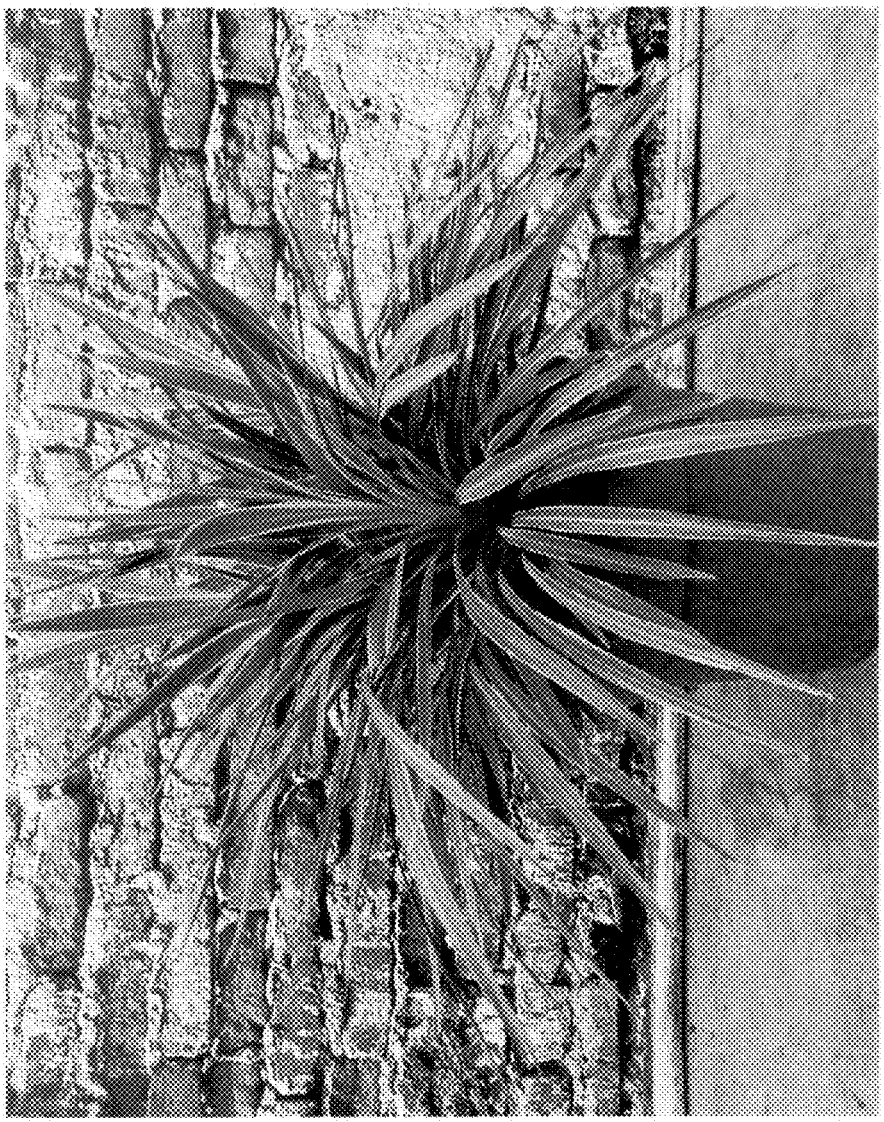
FIG. 1 illustrates in full color a plant of 'TUS020'.
Figure 2:
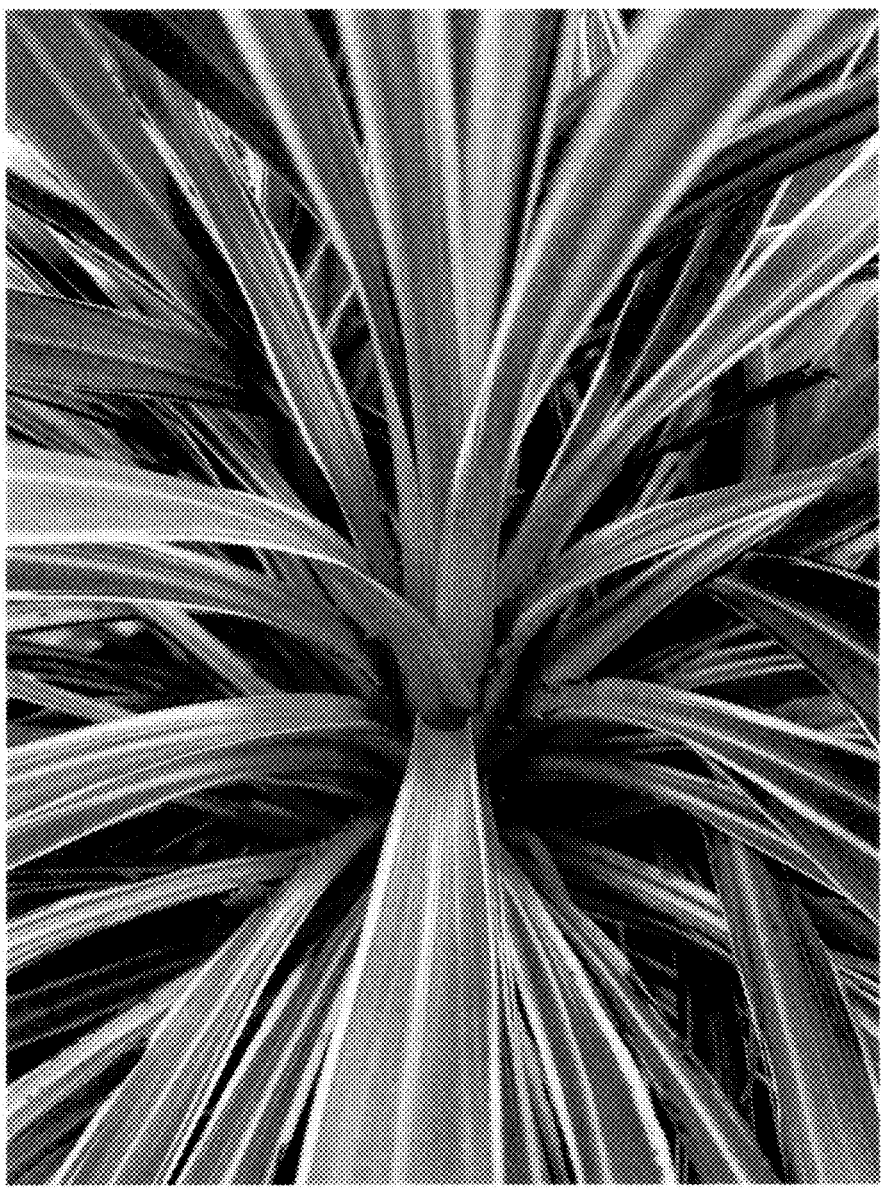
FIG. 2 illustrates in full color a close-up view of the interior of the plant in FIG. 1.
Figure 3:
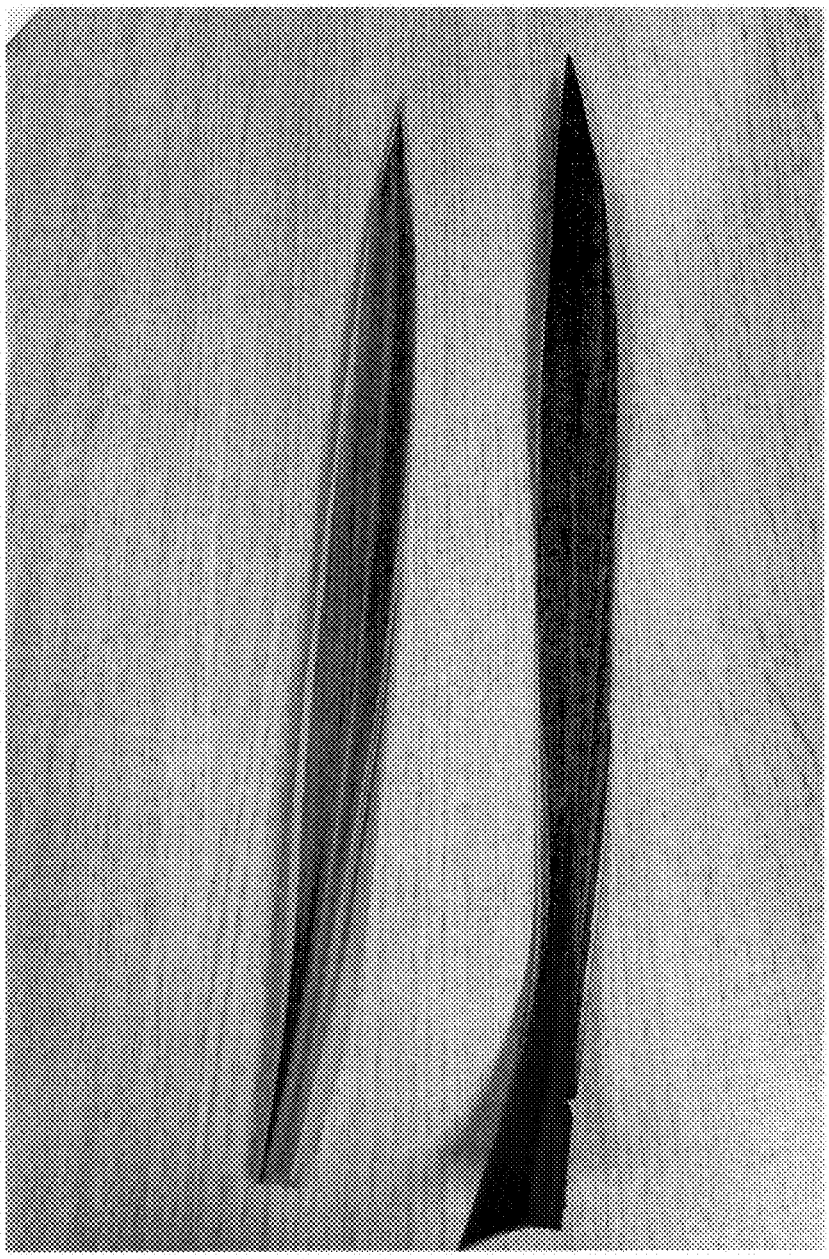
FIG. 3 illustrates in full color both a mature and young leaf of 'TUS020'. The young leaf is on the left; mature leaf is on the right.

In the following description, color references are made to The Royal Horticultural Society Colour Chart 2001, except where general terms of ordinary dictionary significance are used. The following observations and measurements describe 'TUS020' plants grown in a glasshouse in Wenhout, the Netherlands. Growing temperature ranged from about 10° C. to 16° C. at night to 5° C. to 28° C. during the day. No artificial light, photoperiodic treatments or chemical treatments were given to the plants. Measurements and numerical values represent averages of typical flowering types.

Botanical classification: *Cordyline australis* 'TUS020'.

Age of the plant described: Approximately 18 months.

Container size of the plant described: 28 cm.

PROPAGATION

Time to rooting: 3 weeks.

Time from rooted cutting to young plant: 12 to 16 weeks.

PLANT

Plant type: Perennial.

Growth habit: Round, upright, leaves arching.

Height: 50 cm.

Spread: 98 cm.

Growth rate: Moderate.

Stem:

*Quantity.*—1 main stem, without pinching. If pinched, 4 basal stems.

*Color.*—Woody stems RHS Brown N199B 199C and 199D flushed Red 47A and 47B.

*Length.*—3.5 cm.

*Diameter.*—3.5 cm.

*Shape.*—Round.

Branching characteristics: Main shoot from the base; no lateral branching.

FOLIAGE

Leaf:

*Arrangement.*—Alternate, single.

*Length.*—44 cm.

*Width.*—2.3 cm.

*Shape of blade.*—Linear.

*Apex.*—Narrow and long acuminate.

*Base.*—Sessile. Clasping.

*Margin.*—Entire.

*Curvature.*—Weak to medium, more curvature with age.

*Texture of top surface.*—Smooth, glossy.

*Texture of bottom surface.*—Smooth, slightly glossy.

*Color.*—Young, Upper Side: Midrib RHS Yellow-Green 146A, 146B and 146C. Base Red 36A, Orange-Yellow 22B and faded Red 45B and 45C. Veins Red N45A and N45C. Margins Orange-Yellow 22B, with Red-Orange 30A toward base. Young, Under Side: RHS Yellow-Green 146B, 146C and 146D. Toward base, a mix of Orange-Yellow 22A, 22B and faded Red 45B and 45C. Veins Red N45A. Mature, Upper Side: RHS Green 137B, 137C and 137D. Midrib Yellow-Green 145A, 145B and 145C. Margin Yellow 10B and Red 47A. Base Red 47A and 47B, Red 37A, and Red 39A. Mature, Under Side: A mix of RHS Green N137A, N137BB with Yellow-Green 145A, 145B and 145C stripes. Base Red 45A and 45B with N45A and 46A. Margins Yellow 10B.

FLOWER

Flowers not observed to date.

OTHER CHARACTERISTICS

Seeds and fruits: Not observed.

Disease/pest resistance: Similar resistance and susceptibility to normal diseases and pests of *Cordyline* has been observed. Typical pests of *Cordyline* include scale, typically *Icerya puchasi*, mealybugs (various species of *Pseudococcidae*) and spider mites (various species of *Tetranychus*). Disease which may be found in *Cordyline* include Anthracnose (*Collectotrichum*), Armillaria root rot (*Armillaria mellea*) and *Verticillium* wilt (*V. dahlia* and *V. albo-atrum*).

Temperature tolerance: Cold hardy to approximately −5° C.

What is claimed is:

1. A new and distinct cultivar of *Cordyline australis* plant named 'TUS020' as herein illustrated and described.

* * * * *